US008684919B2

(12) United States Patent
Anca et al.

(10) Patent No.: US 8,684,919 B2
(45) Date of Patent: Apr. 1, 2014

(54) MOUTHPIECE AND METHODS OF USE OF SAME

(75) Inventors: Diana Anca, New York, NY (US); Faiz Bohra, New York, NY (US); Darla Gill, Salt Lake City, UT (US); Trent Clegg, Lehi, UT (US); Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 299 days.

(21) Appl. No.: 13/032,070

(22) Filed: Feb. 22, 2011

(65) Prior Publication Data

US 2012/0143003 A1    Jun. 7, 2012

Related U.S. Application Data

(60) Provisional application No. 61/338,665, filed on Feb. 22, 2010.

(51) Int. Cl.
*A61B 1/32* (2006.01)
(52) U.S. Cl.
USPC ........................... 600/239; 600/237
(58) Field of Classification Search
USPC .................. 600/101–183, 185–196, 201–249
See application file for complete search history.

(56) References Cited

U.S. PATENT DOCUMENTS

| | | | |
|---|---|---|---|
| 4,502,478 A | 3/1985 | Lifton | |
| 5,092,314 A * | 3/1992 | Zeitels | 600/194 |
| 5,413,095 A | 5/1995 | Weaver | |
| 5,533,523 A | 7/1996 | Bass, Jr. et al. | |
| 5,649,540 A | 7/1997 | Alvarez et al. | |
| 6,257,238 B1 | 7/2001 | Meah | |
| 6,517,549 B1 | 2/2003 | Dennis | |
| 7,975,689 B2 | 7/2011 | Hauge | |
| 2006/0251694 A1 * | 11/2006 | Nielsen et al. | 424/422 |
| 2007/0006878 A1 | 1/2007 | Mackey et al. | |
| 2007/0113844 A1 | 5/2007 | Garren et al. | |
| 2008/0058606 A1 * | 3/2008 | Miles et al. | 600/214 |
| 2008/0081312 A1 | 4/2008 | Pruss et al. | |
| 2008/0177146 A1 * | 7/2008 | Chen | 600/185 |
| 2010/0030027 A1 | 2/2010 | Bastid et al. | |
| 2010/0262033 A1 * | 10/2010 | Colman et al. | 600/532 |
| 2010/0326435 A1 | 12/2010 | Filipi | |
| 2011/0226239 A1 * | 9/2011 | Hauge | 128/200.26 |

FOREIGN PATENT DOCUMENTS

| | | |
|---|---|---|
| JP | 2008289520 | 4/2008 |
| WO | WO 2008006968 A2 * | 1/2008 |
| WO | WO2009066277 | 5/2009 |

OTHER PUBLICATIONS

International Preliminary Report on Patentability dated Aug. 28, 2012 for PCT/US2011/025652.
Product Brochure—End Leader Multi-Type E by Top Corporation, Japan: Mar. 1, 2008.
The Hauge Airway by Intermed Penton America, Product Phamplet, Available at: www.penlonamerica.com/hauge.htm. Accessed Jan. 5, 2012.

* cited by examiner

*Primary Examiner* — Jerry Cumberledge
*Assistant Examiner* — Nicholas Plionis
(74) *Attorney, Agent, or Firm* — Stoel Rives LLP

(57) ABSTRACT

Various embodiments of mouthpieces for use during endoscopic procedures are disclosed herein. According to various embodiments, a mouthpiece may include a shield, a primary instrument channel, a bite block, an oxygen administration channel and a tongue depressor. The shield, bite block, oxygen administration channel and tongue depressor may be integrally formed.

22 Claims, 11 Drawing Sheets

MOUTHPIECE AND METHODS OF USE OF SAME

RELATED APPLICATIONS

The present application claims the benefit under 35 U.S.C. §119(e) of U.S. Provisional Patent Application No. 61/338,665, filed Feb. 22, 2010, titled "COMBINATION BITE BLOCK, ORAL AIRWAY, AND OXYGEN PORT," which application is incorporated herein by reference in its entirety.

DETAILED DESCRIPTION

Figure 1A:
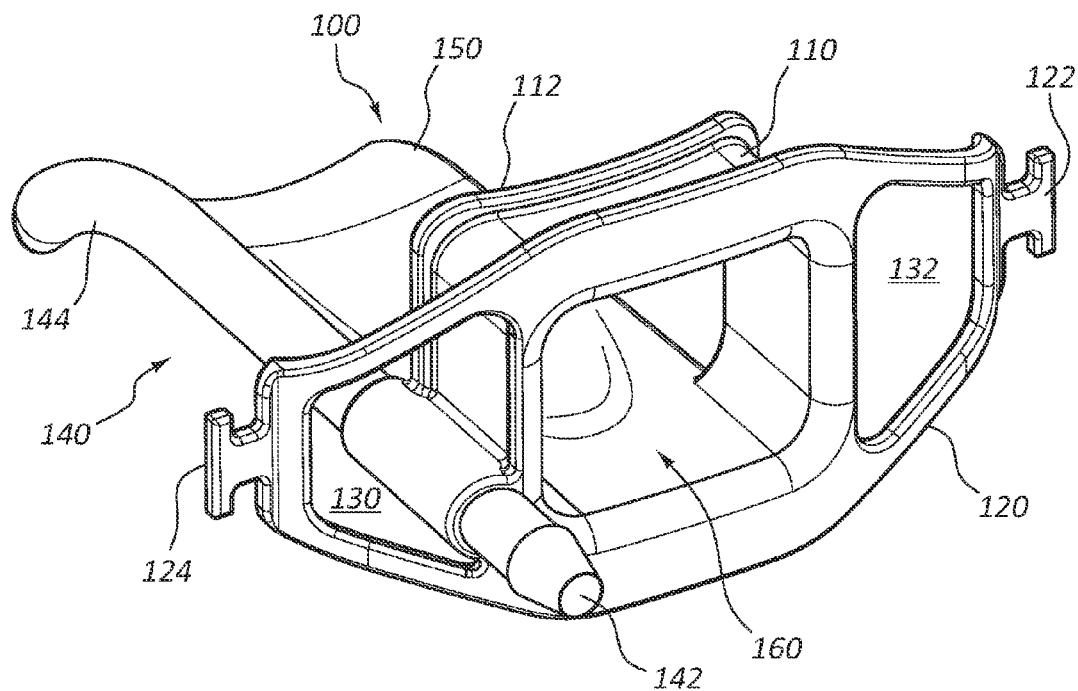
FIG. 1A is an isometric view of one embodiment of a mouthpiece.

Endoscopic procedures may be used to treat and diagnose a wide variety of medical conditions. For example, bronchoscopy is a medical procedure used to diagnose and treat airway pathology. Conditions such as pneumonia, cancer, atelectasis, hemoptysis, and the presence of a foreign object may be diagnosed and/or treated by bronchoscopy. Further, upper endoscopy (also known as esophagogastroduodenoscopy or EGD) is a procedure that enables a doctor to examine, diagnose, and treat conditions of the esophagus, stomach and duodenum (e.g., cancer, an ulcer, the presence of a foreign object, inflammation).

In a bronchoscopy procedure, a bronchoscope is passed through the patient's mouth, and then through the vocal cords into the trachea and bronchi. A patient undergoing bronchoscopy typically lies on his/her back for the procedure, a local anesthetic may be sprayed into the patient's pharynx. A bite block may be placed into the patient's mouth to prevent damage to the scope or the patient's teeth. Bronchoscopy may be accompanied by hypoxia (reduced content of oxygen in blood) and, less commonly, apnea (cessation of respiration).

Similarly, in an endoscopic procedure an endoscope is passed through the patient's mouth and into the patient's upper gastrointestinal tract. During an endoscopic procedure, a doctor may perform biopsies, stop bleeding, remove a foreign object, and perform other tasks. As with bronchoscopy, endoscopy may be accompanied by hypoxia and, less commonly, apnea.

Various embodiments of mouthpieces disclosed herein provide a bite block, an oxygen administration channel, a primary instrument channel, and a tongue depressor. The bite block may be used to keep a patient's mouth open during a procedure and to prevent damage to the patient's teeth or medical instruments that could be caused if the patient were to bite down on the medical instruments in the patient's mouth. According to certain embodiments, apertures may be provided on one or both sides of a bite block in order to allow for additional points of entry for instruments into the patient's mouth.

Many bronchoscopic and endoscopic procedures are performed under general anesthetic. When a patient is placed under general anesthetic, oxygen is frequently administered. During a bronchoscopic or endoscopic procedure, oxygen may be administered via the oxygen administration channel in order to reduce the risk of hypoxia. According to various embodiments, the oxygen administration channel may be configured to deliver oxygen to the posterior pharynx. The tongue depressor may lift and hold the base of the patient's tongue upward and forward (in a supine patient) to provide improved airflow during the procedure.

Certain embodiments may also include a supplemental access port disposed on the opposite side of the mouthpiece from the oxygen administration channel. The supplemental access port may provide an additional point of access for medical tools that may be used during a procedure. For example, the supplemental access port may allow for the use of a suction tube.

According to various embodiments, a mouthpiece may be integrally formed and may be manufactured in a variety of sizes. Further, mouthpieces according to the present disclosure may be provided in a variety of sizes and configurations that are specifically adapted to patients of differing sizes and various types of procedures. For example, in one embodiment, the bite block, tongue blade, and oxygen channel may be sized to accommodate an adult human oral cavity. Further, in another embodiment, the bite block, tongue blade, and oxygen channel have dimensions suitable for human pediatric use. In addition, certain embodiments may have dimensions and shapes suitable for use in non-human mammals.

A primary instrument channel may be formed by the bite block, and the primary instrument channel may have any shape suitable to accommodate medical instruments that are used during a medical procedure. For example, the primary instrument channel may be square, rectangular, or ovoid. According to certain embodiments, the oxygen administration channel may be located outside of the primary instrument channel. Such embodiments may maximize the area available for insertion of medical instruments through the patient's mouth and into the patient's respiratory tract or upper gastrointestinal tract. Further, the oxygen administration channel may be positioned with respect to the bite block such that contact between a patient's teeth and the bite block prevent contact between the oxygen administration channel and the patient's teeth.

FIGS. 1A-1E illustrate various views of one embodiment of a mouthpiece 100. Mouthpiece 100 includes a bite block 110, a shield 120, apertures 130 and 132, an oxygen administration channel 140, a tongue depressor 150, and a primary instrument channel 160. Shield 120 contacts the face and lips of the patient. Bite block 110 is disposed on the posterior side of shield 120. A tongue depressor 150 is also disposed on the posterior and bottom side of bite block 110. Anchors 122 and 124 are disposed on the sides of shield 120. Anchors 122 and 124 are illustrated as "T" shaped. A strap (not shown) can be attached to anchors 122 and 124. The strap may be placed around the back of a patient's head to secure mouthpiece 100 during a procedure. In alternative embodiments, anchors 122 and 124 may be ring shaped and may allow straps to pass through. Furthermore, anchors 122 and 124 may be shaped as slide buckles.

During a procedure, bite block 110 may be positioned such that a patient's teeth and lips are situated between shield 120 and flange 112. Flange 112 may help to prevent mouthpiece 100 from coming out of a patient's mouth during a procedure. Bite block 110 may be configured to permit ease of use and a comfortable fit on the patient. The shield 120 can be made of any material rigid enough to maintain its shape and withstand repeated sterilizations but can also be flexible enough to allow the mouthpiece 100 to bend for the patient's comfort.

Bite block 110 may be made of a material that is rigid enough to keep its shape, and strong enough to withstand without significant deformation from the pressure exerted if the patient bites hard on the bite block 110; however, the material used in the construction of bite block 110 may be soft enough to avoid damage to the patient's teeth. According to some embodiments, a padded collar may be placed around the bite block 110 to provide a softer material for the teeth to contact. According to one embodiment, the material used in the construction of mouthpiece 100 may have a durometer hardness of between 30 Shore A to 65 Shore D.

According to certain embodiments, bite block 110 and other components of mouthpiece 100 may be formed from a variety of materials including polyurethane, polypropylene, polyethylene, silicone, and ABS (acrylonitrile-butadiene-styrene). According to one particular embodiment, a dual injection fabrication technique may be used. Santoprene may be used in connection with such embodiments. Mixtures and blends of the polymers listed above and similar polymers may be used to form a mouthpiece having desired properties. Further, various embodiments may utilize latex free materials and manufacturing processes. A hydrophilic coating may be used on one or more portions of the device.

As illustrated, oxygen administration channel 140 may be disposed adjacent to bite block 110 and outside of primary instrument channel 160. Placement of oxygen administration channel 140 adjacent to bite block 110 protects oxygen administration channel 140 from damage that could be caused if the patient were to bite down on oxygen administration channel 140. Further, by placing oxygen administration channel 140 outside of primary instrument channel 160, more space may be provided for medical instruments in primary instrument channel 160.

Oxygen administration channel 140 includes a forward end extending from the anterior end of shield 120 and configured to engage oxygen tubing using a connector 142. As illustrated in FIG. 1A, connector 142 comprises a pressure connector. In alternative embodiments, a connector may be embodied as a luer lock. Connector 142 may provide an air-tight seal and may be used to provide oxygen to a patient.

Oxygen administration channel 140 may include a tube 144 that extends along at least a portion of the length of tongue depressor 150. According to alternative embodiments, the length of tube 144 may vary with respect to tongue depressor 150 (e.g., in some embodiments, tube 144 may be shorter, longer, or of approximately the same length, as tongue depressor 150). According to one particular embodiment, tube 144 may extend beyond the length of tongue depressor 150 and may be positioned near the trachea. In this position, tube 144 may be used to provide jet ventilation. In one embodiment in which tube 144 extends beyond tongue depressor 150, an attachment of a desired length may be connected to tube 144. The diameter of tube 144 and connector 142 may be such that a sufficient volume of gas can be provided to supplement the patient's respiration. In addition, oxygen administration channel 140 may provide a route for topical administration of anesthesia to a patient's pharyngeal region. According to one embodiment, connector 142 may be formed of a rigid material that allows connector 142 to properly engage the tubing, while at least of portion of tube 144 is formed of a more flexible material that allows tube 144 to enter the patient's pharynx. Tube 144 and connector 142 may be circular or oblong (e.g., partially flattened in one dimension) in cross-section.

Tongue depressor 150 may be substantially rigid and have a downward curve that is configured to depress the patient's tongue. Further, tongue depressor 150 may act as a guide for instruments inserted through primary instrument channel 160. Tongue depressor 150 may prevent the retraction of the forward portion of the patient's tongue, which could cause a blockage of the patient's airway. Tongue depressor 150 may have a width such that it fits between the rear teeth of the patient. According to various embodiments, mouthpiece 100 may be color-coded based on the size of tongue depressor 150, according to standard color schemes used for oral airways according to the length of tongue depressor 150.

According to certain embodiments, tongue depressor 150 may be impregnated with a local anesthetic. Further, the local anesthetic could be slowly released over a period time. The period of time may correspond to an anticipated length of time required for a medical procedure involving mouthpiece 100.

Mouthpiece 100 may be used in connection with a method for performing endoscopy, which includes the steps of inserting mouthpiece 100 into a patient's oral cavity; administering oxygen through oxygen administration channel 140; and passing an endoscope (not shown) through primary instrument channel 160. Further steps may include administering topical anesthesia to the patient through oxygen administration channel 140 or through a supplemental access port (not shown).

Mouthpiece 100 may also be used in connection with a method for performing bronchoscopy, which includes inserting mouthpiece 100 into a patient's oral cavity; administering oxygen through the oxygen administration channel 140; and passing a bronchoscope (not shown) through primary instrument channel 160. Further steps may include administering topical anesthesia to the patient through oxygen administration channel 140 or through a supplemental access port (not shown).

According to various embodiments, primary instrument channel 160 may be at least partially defined by shield 120 and by bite block 110. Primary instrument channel 160 may be configured in a variety of shapes. In the embodiment illustrated in FIGS. 1A-1D, primary instrument channel 160 is approximately square-shaped with rounded corners. In other embodiments, primary instrument channel 160 may be round, oval, elliptical, rectangular, etc.

Figure 1B:
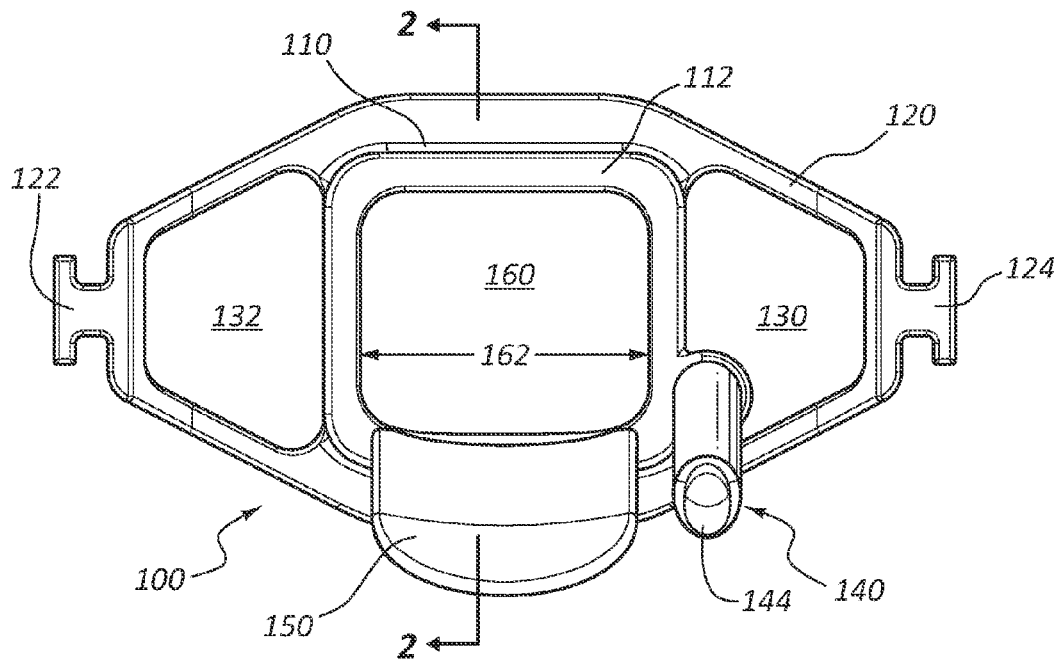
FIG. 1B is a rear view of the mouthpiece illustrated in FIG. 1A.
Figure 1C:
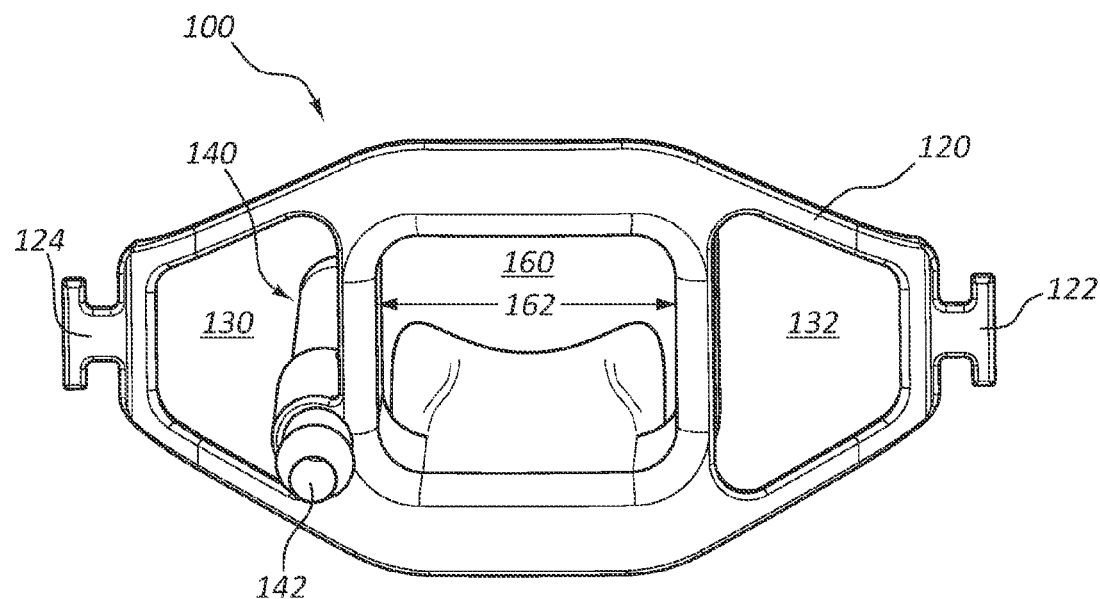
FIG. 1C is a front view of the mouthpiece illustrated in FIG. 1A.

FIGS. 1B and 1C illustrate mouthpiece 100 from a rear perspective and a front perspective, respectively. As illustrated in these figures, primary instrument channel 160 extends through shield 122 and bite block 110 to allow the passage of instruments into the patient's pharynx. Primary instrument channel 160 may have a size and shape that facilitates the passage of instruments used in endoscopic and bronchoscopic procedures. A range of sizes may be offered to accommodate patients of different sizes (e.g., a smaller size for a child and a larger size for an adult). The size of primary instrument channel 160 may be given in terms of a diameter or width 162, or may be given on the French scale, where the French gauge is equal to 3 times diameter 162, as shown in Eq. 1.

$$\text{French Gauge} = \text{Diameter (mm)} \times 3 \qquad \text{Eq. 1}$$

According to one embodiment, primary instrument channel 160 may be between 40 French and 84 French (13.33 mm and 28 mm). According to another embodiment, primary instrument channel 160 may be between 50 French and 65 French (16.67 mm and 21.67 mm). Finally, according to yet another embodiment, primary instrument channel 160 may be approximately 60 French (20 mm).

Shield 120 may define apertures 130 and 132, which may provide additional areas of access to a patient's mouth. In the illustrated embodiment, oxygen administration channel 140 is disposed in aperture 130; however, additional area in aperture 130 is available for access to the patient's mouth. Apertures 130 and 132 may be used to introduce a suction tube or other instrument into a patient's mouth. Apertures 130 and 132 may be formed in any desired shape. In the illustrated embodiment, apertures 130 and 132 are approximately trapezoidal with rounded corners.

Figure 1D:
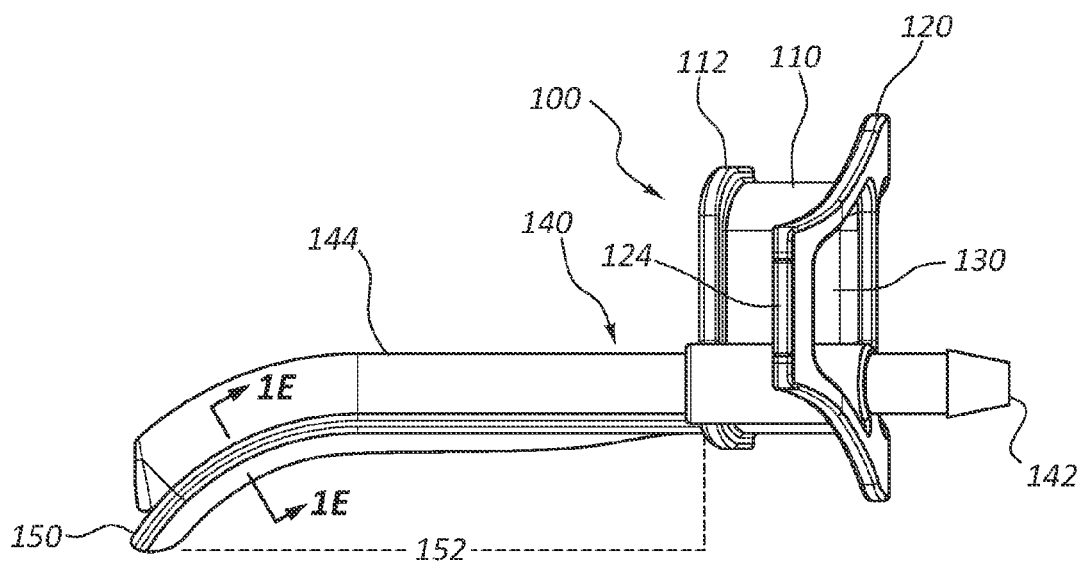
FIG. 1D is a side view of the mouthpiece illustrated in FIG. 1A.

FIG. 1D illustrates a side view of mouthpiece 100. As illustrated in FIG. 1D, bite block 110 is significantly thicker than shield 120. According to one embodiment, bite block 110 may be between 5 and 10 times thicker than shield 120. As discussed above, mouthpiece 100 may be integrally formed. Accordingly, for a given material used to form shield 120 and bite block 110, shield 120 may have greater flexibility due to its reduced thickness, and bite block 110 may have increased rigidity due to its increased thickness. The thickness of shield may be selected such that shield 120 is sufficiently rigid to provide support for a strap (not shown) while being flexible for improved patient comfort.

FIG. 1D also illustrates that tongue depressor 150 has a length 152. Various embodiments may include a variety of lengths 152. As illustrated in FIG. 1D, the length of tongue depressor 150 is measured from the posterior side of bite block 110. Length 152 may be adapted based on a patient's age (e.g., adult or child) and/or size (small, medium, or large). According to one embodiment, length 152 may be between 40 and 140 mm. According to another embodiment, length 152 may be between 90 and 120 mm. Finally, according to yet another embodiment, length 152 may be approximately 110 mm.

As illustrated in FIGS. 1A-1D, the center of shield 120, the center of bite block 110, and the center of primary instrument channel 160 all lie along the same axis. While a coaxial arrangement is illustrated, according to various embodiments, the centers of one or more of shield 120, bite block 110 and primary instrument channel 160 may not be coaxial.

Figure 1E:
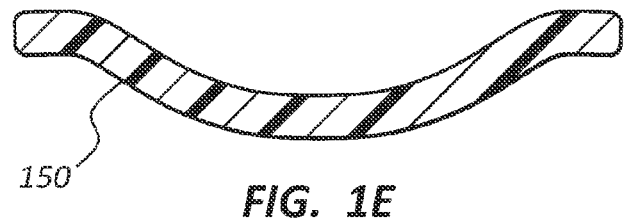
FIG. 1E is a cross-sectional view taken along the line 1E-1E of the mouthpiece illustrated in FIG. 1B.

FIG. 1E is a cross sectional view taken along line 1E-1E in FIG. 1B. As illustrated in FIG. 1E, tongue depressor 150 may have a shallow C-shaped cross-section at least along a portion of its length, such that the shape of tongue depressor 150 approximately matches the curvature of the patient's tongue.

Figure 2:
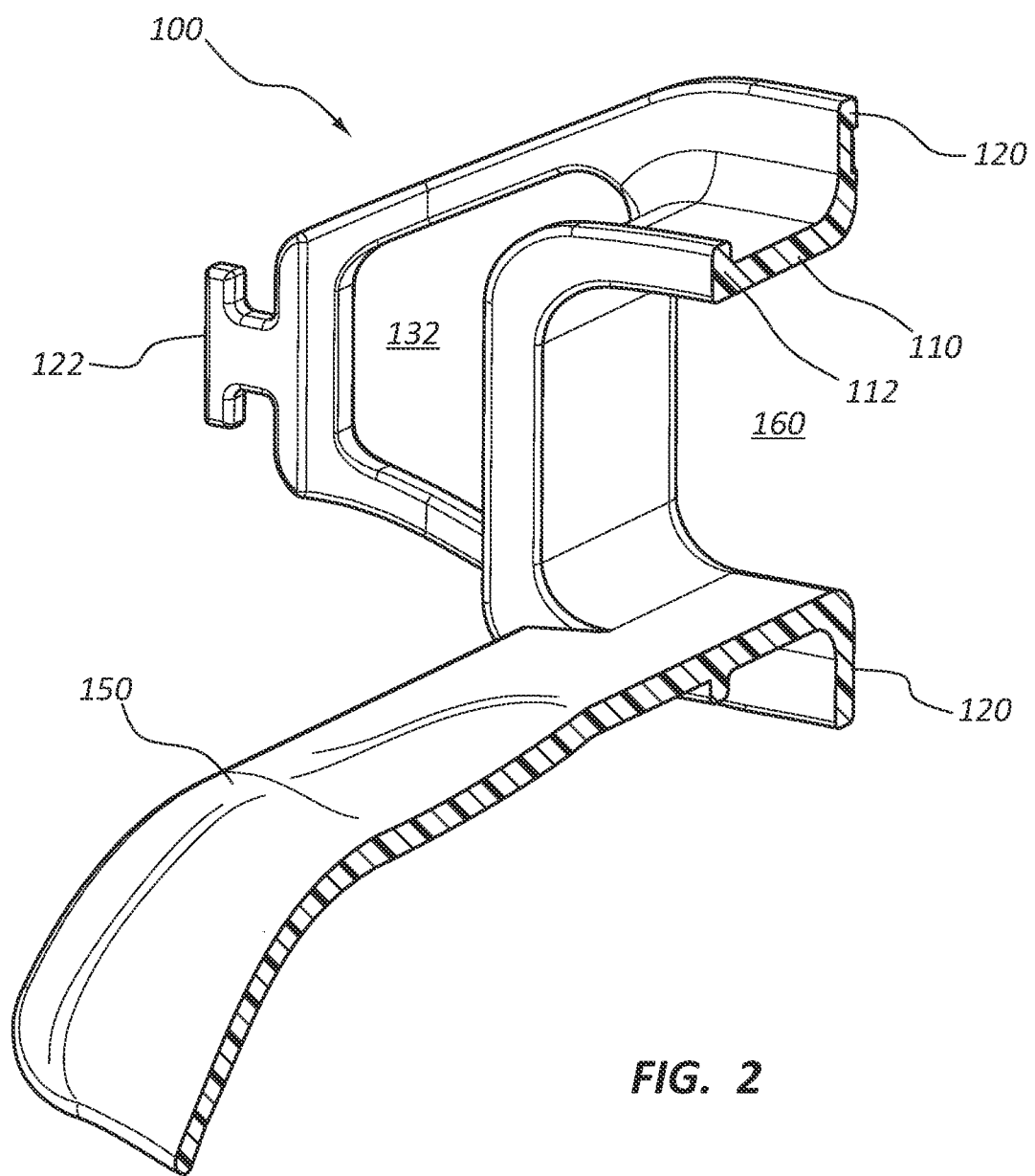
FIG. 2 is a cross-sectional view taken along the line 2-2 of the mouthpiece illustrated in FIG. 1B.

FIG. 2 illustrates a cross-sectional view of mouthpiece 100 taken along line 2-2 in FIG. 1B. FIG. 2 illustrates an embodiment in which mouthpiece 100 is a unitary structure. In other words, individual components that comprise mouthpiece 100 are integrally formed from a single piece of material. The embodiment illustrated in FIG. 2 shows various integrally formed components of mouthpiece 100, including bite block 110, flange 112, shield 120, anchor 122, and tongue depressor 150. Further, primary instrument channel 160 and aperture 132 are also formed by the unitary structure. As an all-in-one device, mouthpiece 100 does not present a risk of dislodgment of any individual component.

Figure 3:
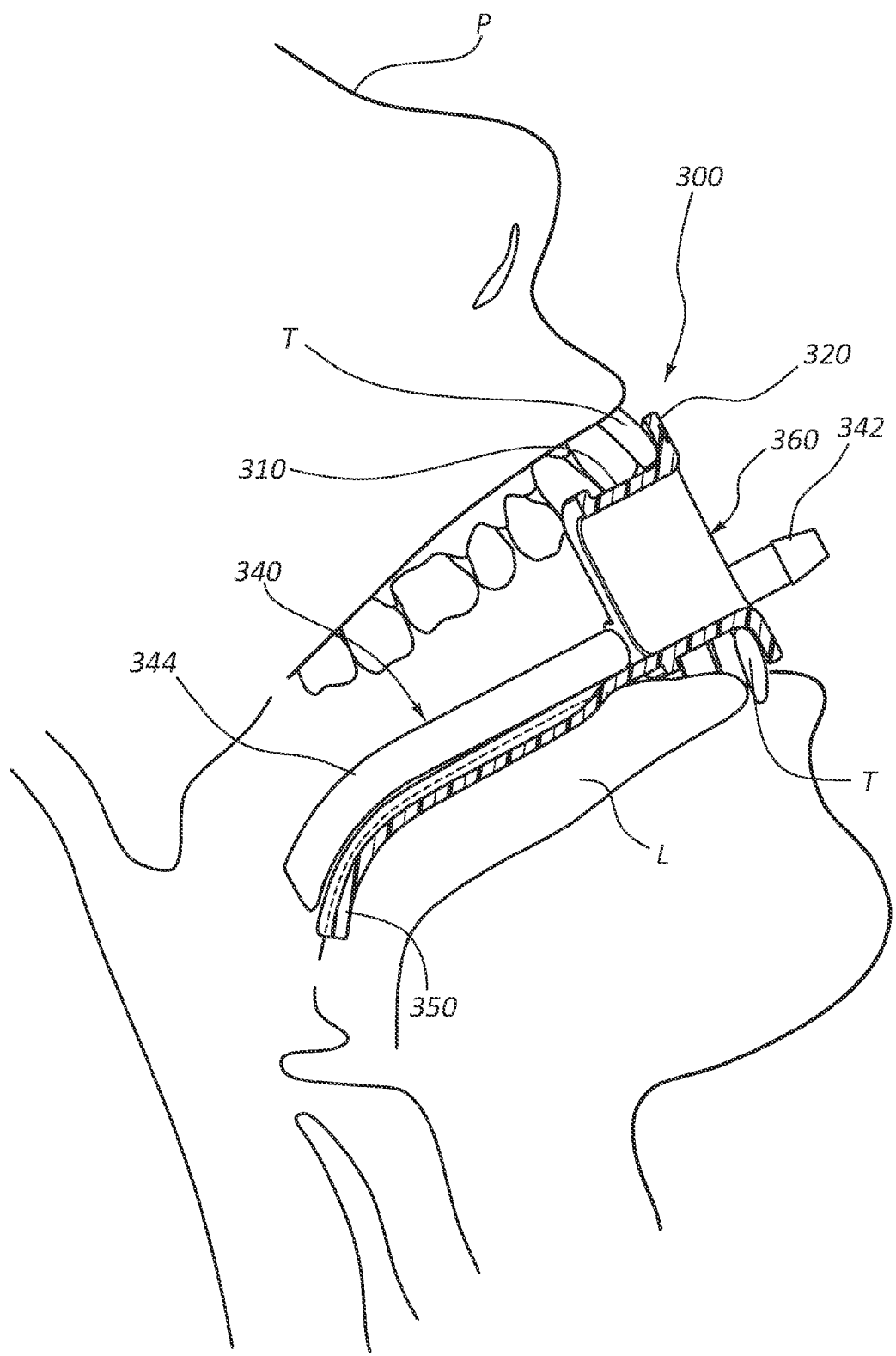
FIG. 3 is a side view of one embodiment of a mouthpiece in a patient's mouth.

FIG. 3 illustrates a view of one embodiment of a mouthpiece 300 in a patient's mouth. As illustrated, a bite block 310 may be in contact with the patient's teeth and may prevent the patient from biting down on medical instruments inserted into the patient's mouth during a procedure. A shield 320 is disposed against the exterior of the patient's mouth. In embodiments including a flange (not shown), the flange may be positioned behind the patient's teeth.

Mouthpiece 300 also includes an oxygen administration channel 340 and a tongue depressor 350. Oxygen administration channel 340 includes a connector 342 and a tube 344. Oxygen administration channel 340 may be positioned to deliver oxygen to the patient's pharyngeal area. Tongue depressor 350 may be configured to prevent the retraction of the forward portion of the patient's tongue, which could cause a blockage of the patient's airway. Tongue depressor 350 may have a width such that it fits between the rear teeth of the patient. Mouthpiece 300 may also include a primary instrument channel 360 through which medical instruments may be inserted into the patient's mouth.

FIGS. 4A-4D illustrate various views of an embodiment of a mouthpiece 400 that includes an oxygen administration channel 440 that is attached to a tongue depressor 450 and integral with a portion of a bite block 410. Mouthpiece 400 includes many features that are similar to the features illustrated in FIGS. 1A-1E and described above, including a bite block 410, a flange 412, a shield 420, a connector 442, a tube 444, anchors 422 and 424, and apertures 430 and 432.

Figure 4A:
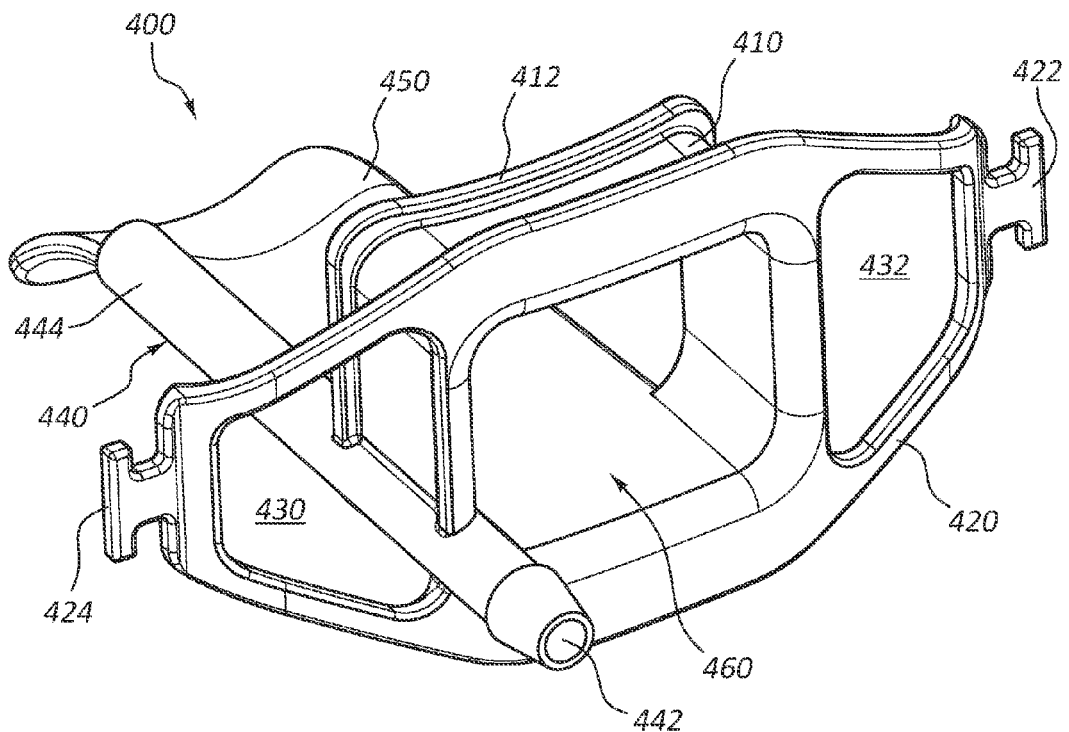
FIG. 4A is an isometric view of one embodiment of a mouthpiece.

As illustrated in FIG. 4A, tube 444 is partially integrated into bite block 410. At the intersection of tube 444 and bite block 410, flange 412 is not present. Such a configuration may allow for additional access to a patient's mouth using aperture 430 while minimizing the amount of space utilized by oxygen administration channel 440 in a primary instrument channel 460.

Figure 4B:
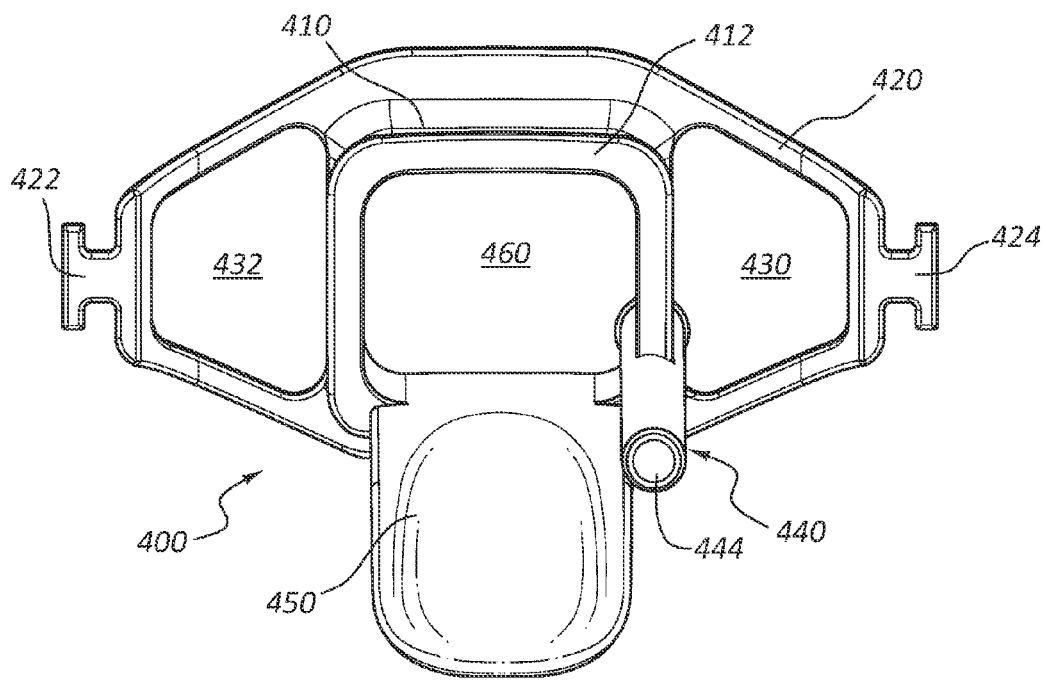
FIG. 4B is a rear view of the mouthpiece of FIG. 4A.
Figure 4C:
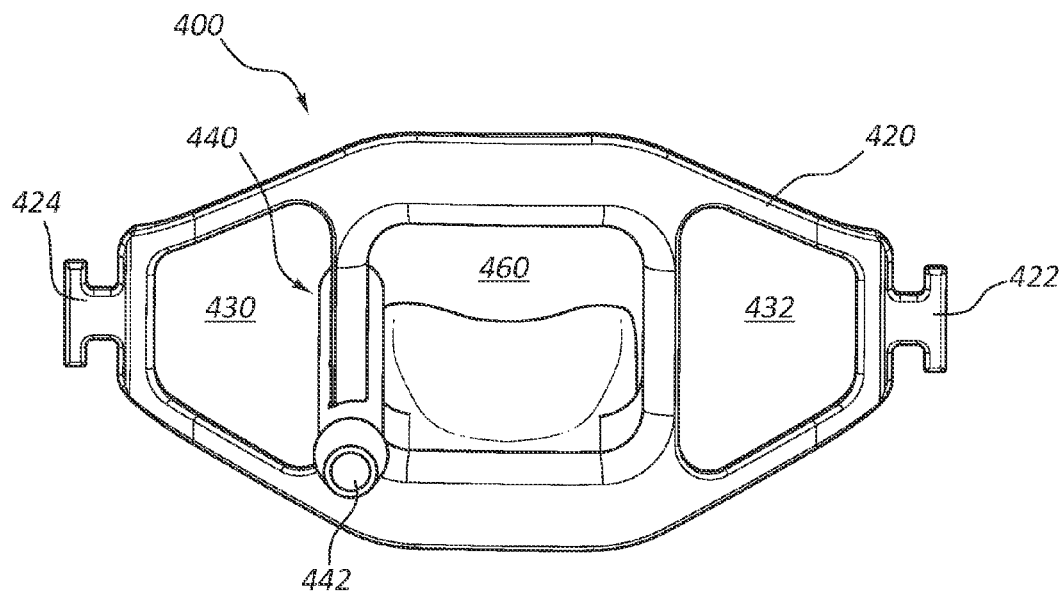
FIG. 4C is a front view of the mouthpiece of FIG. 4A.
Figure 4D:
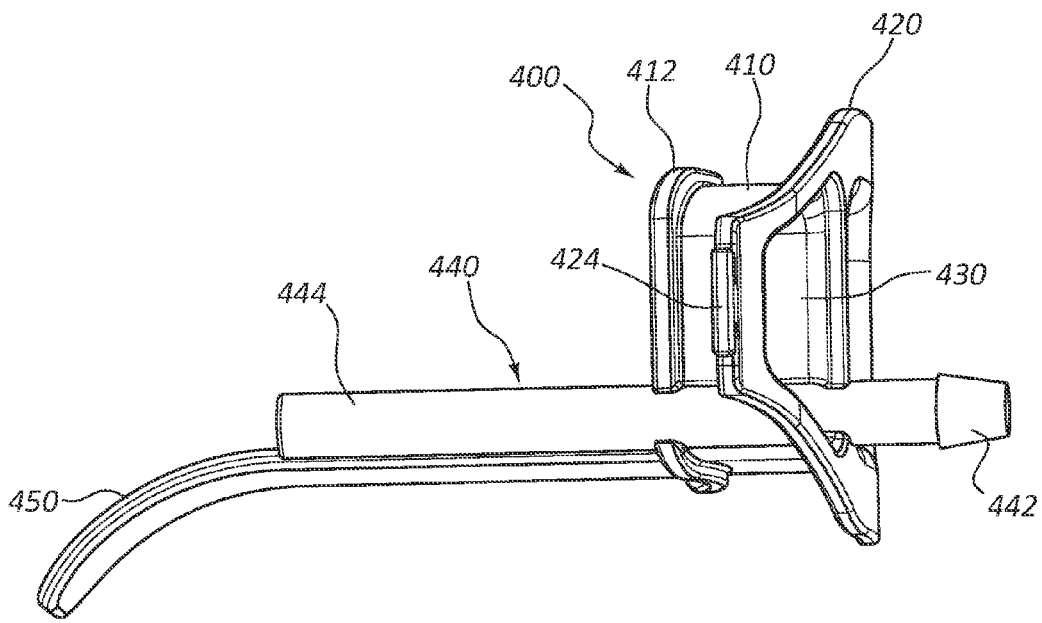
FIG. 4D is a side view of the mouthpiece of FIG. 4A.

FIGS. 4B and 4D illustrate that tube 444 is integrally formed with tongue depressor 450, and show that in the illustrated embodiment, tongue depressor 450 is longer than tube 444. According to alternative embodiments, the length of tube 444 may vary with respect to tongue depressor 450 (e.g., in some embodiments, tube 444 may be shorter, longer, or of approximately the same length, as tongue depressor 450).

FIG. 4C illustrates a front view of mouthpiece 400. As described above, oxygen administration channel 440 is partially integrated with bite block 410; however, only a small amount of space is used by oxygen administration channel 440 in primary instrument channel 460.

Figure 5:
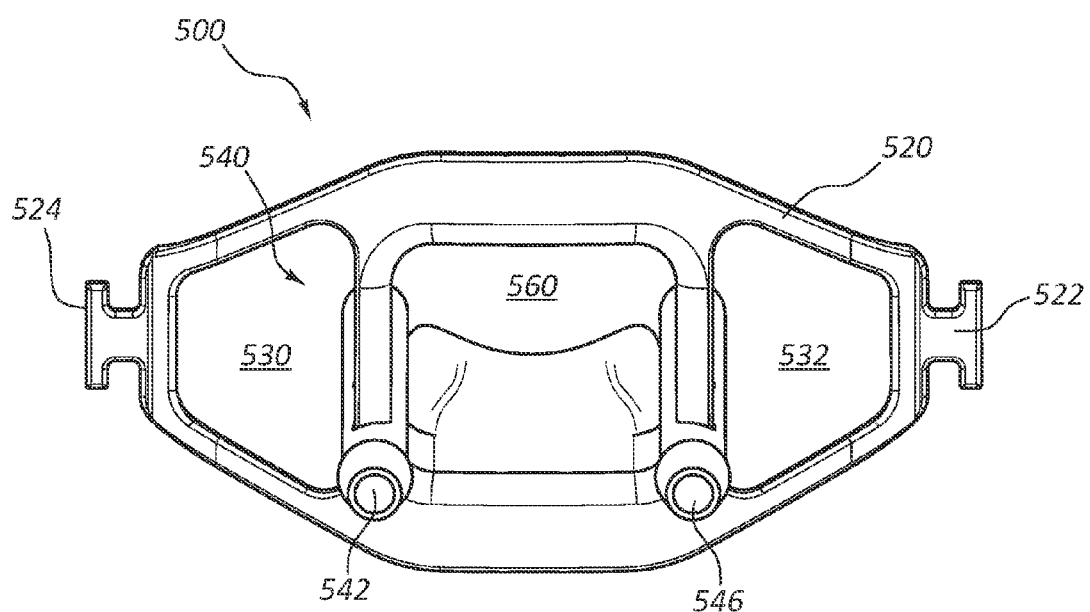
FIG. 5 is a front view of one embodiment of a mouthpiece including an oxygen administration channel and a supplemental port.

FIG. 5 illustrates a front view of one embodiment of a mouthpiece 500 that includes an oxygen administration channel 540 and a supplemental port 546. Mouthpiece 500 includes many features that are similar to the features illustrated in FIGS. 1A-1E as described above, including a shield 520, anchors 522 and 524, apertures 530 and 532, and an oxygen administration channel 540 that includes a connector 542. Mouthpiece 500 also includes a supplemental port 546. Supplemental port 546 may be used for a variety of functions, including providing suction in a patient's mouth, application of topical anesthetic, or introduction of medical instruments into the patient's mouth. In one embodiment, supplemental port 546 may be manipulated into different positions. In another embodiment, supplemental port 546 remains stationary. Further, supplemental port 546 may be used to nebulize a local anesthetic.

Figure 6A:
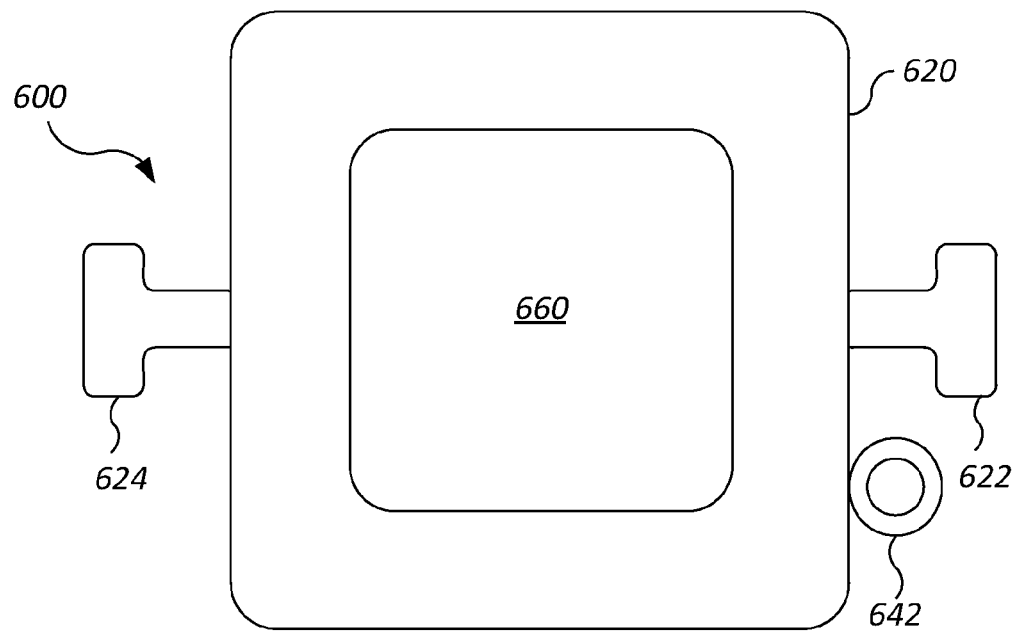
FIG. 6A is a front view of one embodiment of a mouthpiece.
Figure 6B:
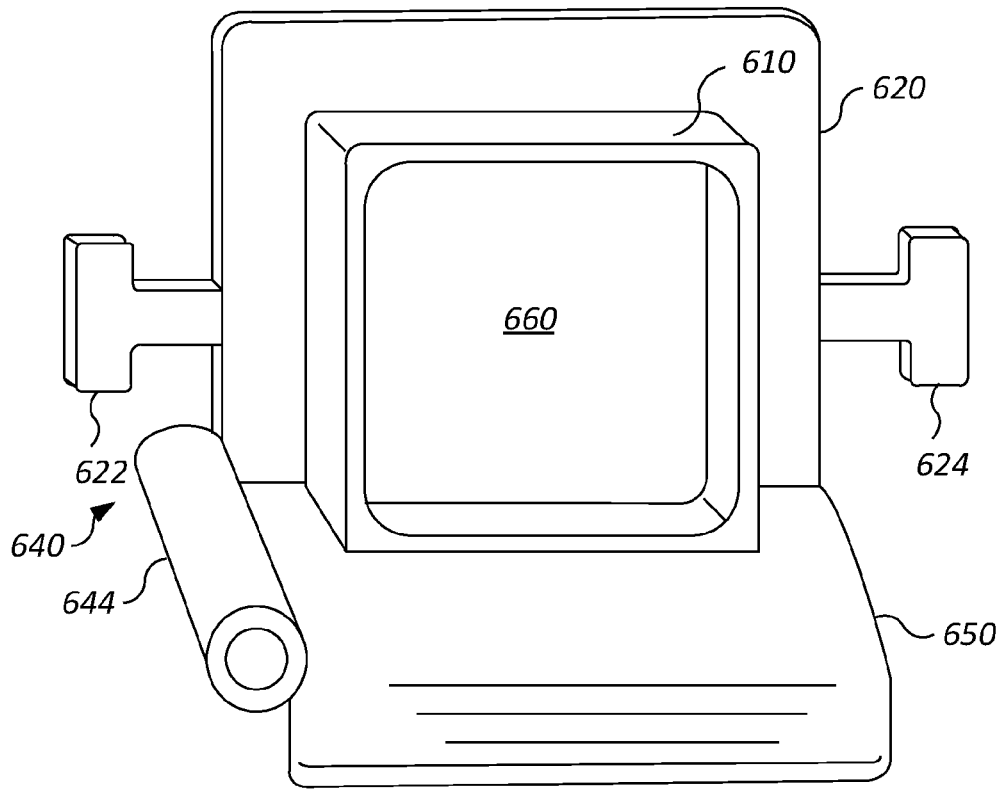
FIG. 6B is a rear view of the mouthpiece of FIG. 6A.

FIG. 6A illustrates a front view of one embodiment of a mouthpiece 600. Mouthpiece 600 includes a shield 620 that contacts the face and lips of the patient. On the posterior side of the shield 620 is disposed a bite block 610, as shown in FIG. 6B. Anchors 622 and 624 are disposed on the sides of shield 620. An oxygen administration channel 640 is also disposed on one side of shield 620 and bite block 610. Oxygen administration channel may comprise a connector 642 and a tube 644. Shield 620 and bite block 610 each at least partially define a primary instrument channel 660 through which medical instruments may be inserted into a patient's mouth. FIGS. 6A and 6B illustrate mouthpiece 600 as having a square shape. Shield 620, according to various embodiments, may be made of any material that is sufficiently rigid to maintain its shape and withstand repeated sterilizations while remaining sufficiently flexible, in order to allow mouthpiece 100 to bend for the patient's comfort.

Figure 6C:
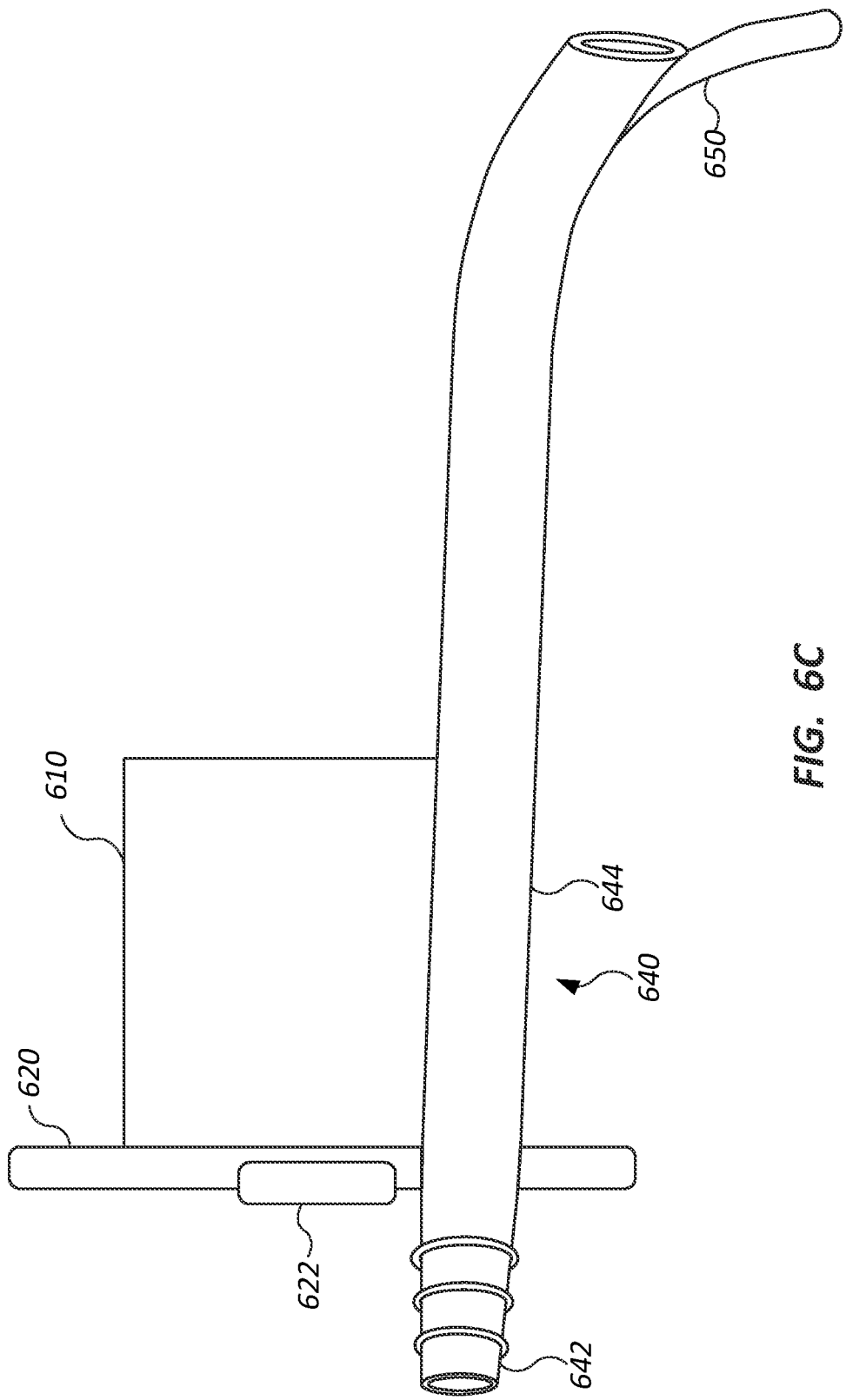
FIG. 6C is a side view of the mouthpiece of FIG. 6A.

FIG. 6C illustrates a side view of mouthpiece 600. Bite block 610 extends from the posterior side of shield 620. Tongue depressor 650 extends rearward from the bottom of bite block 610. Tongue depressor 650 may include a shallow C-shaped cross-section along the contour of the tongue that provides a smooth transition from the square edge of bite block 610. Tongue depressor 650 may be substantially rigid and may have a downward curve that is configured to depress the patient's tongue and act as a guide for instruments inserted through primary instrument channel 660.

Oxygen administration channel 640 is disposed on one side of bite block 610. Oxygen administration channel 640 includes a connector 642 that is configured to engage with tubing. A tube may be in communication with connector 642 and may direct a flow of oxygen toward the pharynx of the patient.

Figure 7:
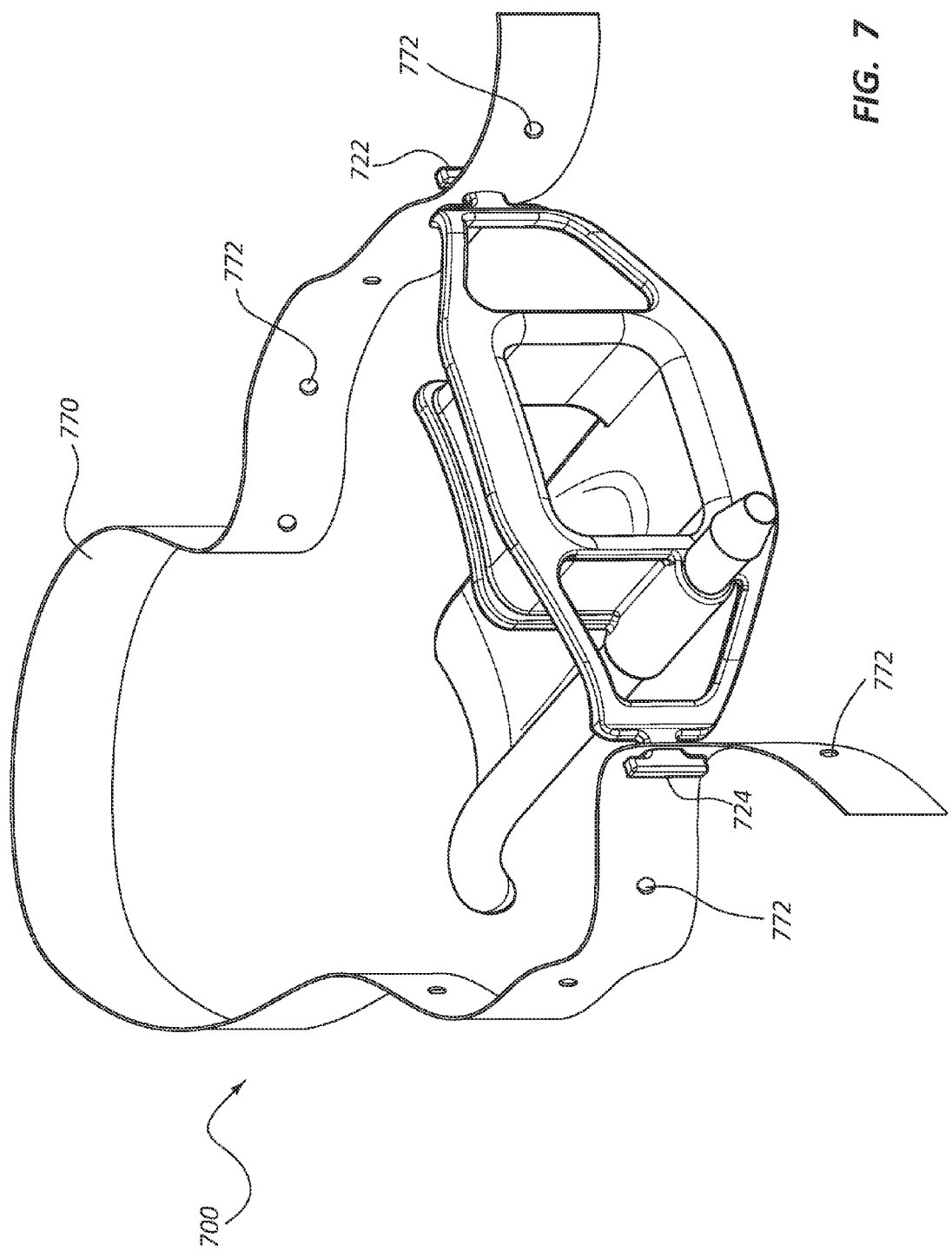
FIG. 7 is a perspective view of one embodiment of a mouthpiece including a strap that may be used to secure the mouthpiece during a medical procedure.

FIG. 7 is a perspective view of one embodiment of a mouthpiece 700 including a strap 770. Strap 770 may be placed around the back of a user's head in order to secure mouthpiece 700 during a medical procedure. Strap 770 includes a plurality of holes 772 that may be used to secure strap 770 to anchors 722 and 724. The plurality of holes 772 may facilitate adjusting the strap based on the size of the patient's head. Strap 700 may be relatively wide for the patient's comfort and to avoid entanglement of the patient's hair and the strap 770. According to alternative embodiments, quick-release latches may be used in place of anchors 722 and 724. In addition to anchors and quick-release latches, other types of strap securing elements may be provided. According to various embodiments, strap 770 may be latex free.

Figure 8A:
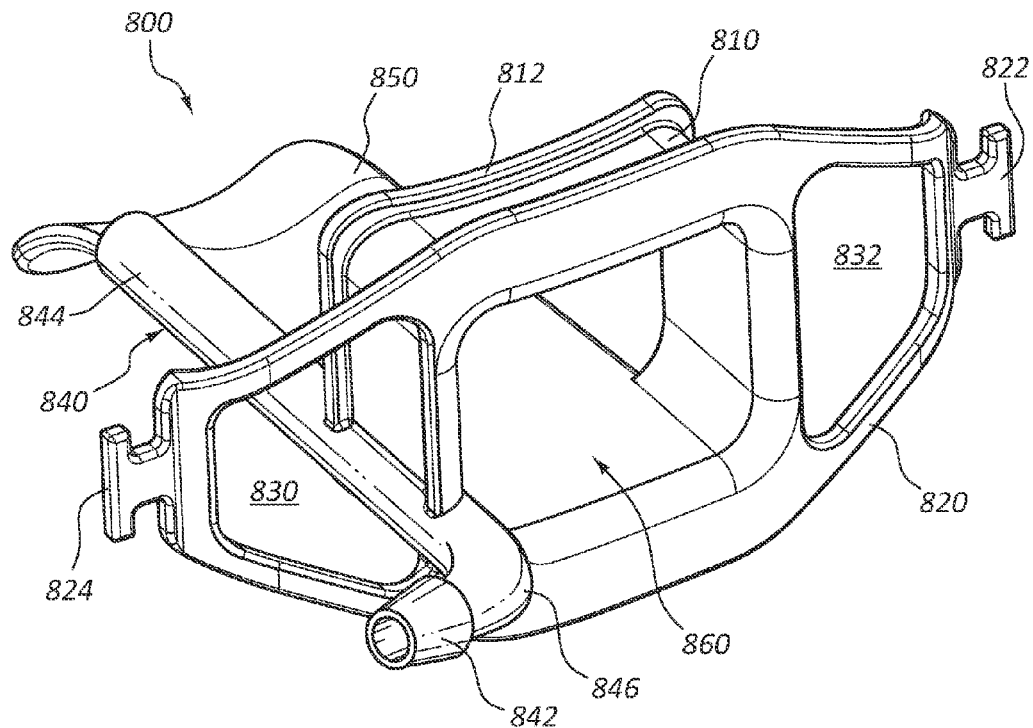
FIG. 8A illustrates a perspective view of one embodiment of a mouthpiece including an oxygen administration channel with a connector that is angled away from a primary instrument channel.

FIG. 8A illustrates a perspective view of one embodiment of a mouthpiece 800 including an oxygen administration channel 840 with a connector 842 that is angled away from a primary instrument channel 860. As discussed above, one or more medical instruments may be inserted into a patient's mouth through primary instrument channel 860. Further, a doctor may manipulate the instruments in order to complete the procedure. The area around primary instrument channel 860 may become crowded, and accordingly, it may be desirable to angle connector 842 away from primary instrument channel 860. Angling connector 842 away from primary instrument channel 860 may help to prevent entanglement of an oxygen tube (not shown) with medical instruments (not shown) being used or manipulated during a medical procedure.

Mouthpiece 800 allows for an oxygen tube (not shown) to be connected from the side, such that the tube is moved away from primary instrument channel 860. Oxygen administration channel also includes an elbow 846 that is connected to a tube 844. According to various embodiments, elbow 846 may have an angle between approximately 30° and approximately 90°. As illustrated in FIG. 8A, elbow 846 and connector 842 may be integrally formed with other components of mouthpiece 800 in order to create a unitary structure. Mouthpiece 800 may also include many additional features that are similar to the features illustrated in FIGS. 1A-1E and that are described above, including a bite block 810, a flange 812, a shield 820, anchors 822 and 824, a tongue depressor 850, and apertures 830 and 832.

Figure 8B:
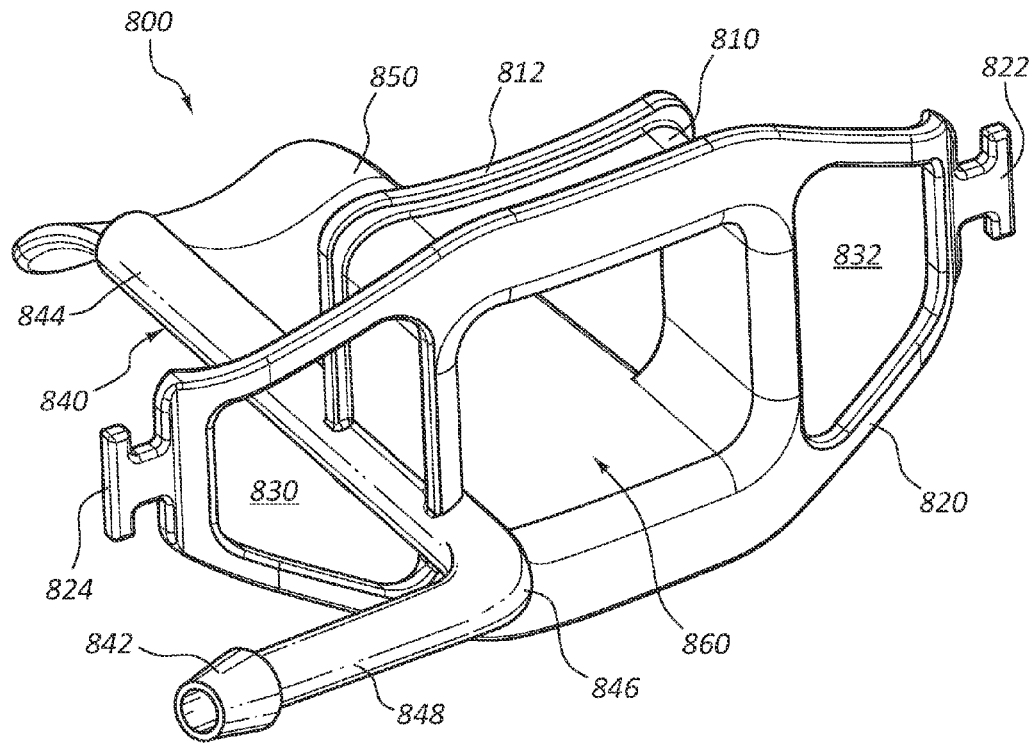
FIG. 8B illustrates a perspective view of one embodiment of a mouthpiece including an oxygen administration channel with an extension tube and a connector that are angled away from a primary instrument channel.

FIG. 8B illustrates a perspective view of mouthpiece 800, as illustrated in FIG. 8A, with the addition of an extension tube 848 disposed between elbow 846 and connector 842. Extension tube 848 may allow for connector 842 to be extended a desired distance from primary instrument channel 860. Providing additional distance between connector 842 and primary instrument channel 860 may help to prevent entanglement of an oxygen tube (not shown) with medical instruments (not shown) being used or manipulated during a medical procedure. Although FIG. 8B illustrates extension tube 848 being integrally formed with tube 844, elbow 846, and connector 842, according to alternative embodiments, extension tube 848 and/or connector 842 may be bonded to mouthpiece 800.

Many changes may be made to the details of the above-described embodiments without departing from the underlying principles of the present disclosure. The scope of the present invention should, therefore, be determined only by the following claims.

The invention claimed is:

1. A mouthpiece configured to be inserted into a patient's mouth during a medical procedure, the mouthpiece comprising:
   a shield configured to contact at least a portion of the patient's face;
   a primary instrument channel at least partially defined by the shield;
   a bite block at least partially defining the primary instrument channel, the bite block configured to contact the patient's teeth and to maintain the patient's mouth in an open position during the medical procedure, the bite block comprising an oxygen administration channel that extends as a straight tube, such that contact between the bite block and the patient's teeth prevents contact between the oxygen administration channel and the patient's teeth;
   a tongue depressor comprising a straight portion extending from a bottom of the bite block followed by a curved portion, wherein the oxygen administration channel extends parallel and adjacent to the straight portion of the tongue depressor, wherein the oxygen administration channel ends prior to the curved portion of the tongue depressor, wherein a length of the tongue depressor is between 40 mm and 140 mm; and
   wherein the shield, the bite block, the oxygen administration channel, and the tongue depressor are integrally formed.

2. The mouthpiece of claim 1, wherein the primary instrument channel comprises an opening between 50 French gauge and 65 French gauge.

3. The mouthpiece of claim 1, wherein at least a portion of the mouthpiece comprises a hydrophilic coating.

4. The mouthpiece of claim 1, wherein the bite block has a durometer hardness of between 30 shore A and 65 shore D.

5. The mouthpiece of claim 1, wherein at least a portion of the tongue depressor comprises a shallow C-shaped cross-section.

6. The mouthpiece of claim 1, wherein the oxygen administration channel is completely disposed outside of the primary instrument channel.

7. The mouthpiece of claim 1, wherein the oxygen administration channel is at least partially disposed outside of the primary instrument channel.

8. The mouthpiece of claim 1, wherein the shield defines a first aperture.

9. The mouthpiece of claim 8, wherein the shield further defines a second aperture and a supplemental access port extends through the second aperture.

10. The mouthpiece of claim 8, wherein the first aperture is approximately trapezoidal.

11. The mouthpiece of claim 1 wherein the bite block further comprises a flange disposed at least partially around its perimeter and configured to be positioned behind the patient's teeth during the medical procedure.

12. The mouthpiece of claim 1, wherein a length of the tongue depressor is between 90 mm and 120 mm.

13. The mouthpiece of claim 1, wherein the mouthpiece is color-coded based on a length size of the tongue depressor.

14. The mouthpiece of claim 1, further comprising a plurality of strap securing elements disposed on opposite sides of the mouthpiece and configured to secure a strap to the mouthpiece.

15. The mouthpiece of claim 14, wherein the plurality of strap securing elements comprises at least one of a T-shaped anchor, a quick-release latch, and a buckle.

16. The mouthpiece of claim 1, wherein the oxygen administration channel comprises:
a connector; and
a tube in communication with the connector, the tube connected to the tongue depressor along at least a portion of its length.

17. The mouthpiece of claim 16, wherein the oxygen administration channel further comprises:
an elbow disposed between the connector and the tube, the elbow configured to angle the connector away from the primary instrument channel.

18. The mouthpiece of claim 17, further comprising:
an extension tube disposed between the elbow and the connector.

19. The mouthpiece of claim 1, wherein the mouthpiece comprises at least one of polyurethane, polypropylene, polyethylene, silicone, ABS, and santoprene.

20. A mouthpiece configured to be inserted into a patient's mouth during a medical procedure, the mouthpiece comprising:
a shield configured to contact at least a portion of the patient's face, the shield defining an aperture;
a primary instrument channel at least partially defined by the shield;
a bite block at least partially defining the primary instrument channel, the bite block configured to contact the patient's teeth and to maintain the patient's mouth in an open position during the medical procedure, the bite block comprising an oxygen administration channel that extends as a straight tube, wherein the oxygen administration channel is completely disposed outside of the primary instrument channel, such that contact between the bite block and the patient's teeth prevents contact between the oxygen administration channel and the patient's teeth;
a tongue depressor comprising a straight portion extending from a bottom of the bite block followed by a curved portion, wherein the oxygen administration channel extends parallel and adjacent to the straight portion of the tongue depressor, wherein the oxygen administration channel ends prior to the curved portion of the tongue depressor, wherein a length of the tongue depressor is between 40 mm and 140 mm;
wherein the oxygen administration channel comprises:
a connector; and
a tube in communication with the connector, the tube connected to the tongue depressor along at least a portion of its length; and
wherein the shield, the bite block, the oxygen administration channel, and the tongue depressor are integrally formed.

21. A method for performing a medical procedure, comprising:
inserting a mouthpiece into a patient's mouth, the mouthpiece comprising:
a shield configured to contact at least a portion of the patient's face;
a primary instrument channel;
a bite block at least partially defining the primary instrument channel, the bite block configured to contact the patient's teeth and to maintain the patient's mouth in an open position during the medical procedure, the bite block comprising an oxygen administration channel that extends as a straight tube, such that contact between the bite block and the patient's teeth prevents contact between the oxygen administration channel and the patient's teeth; and
a tongue depressor comprising a straight portion extending from a bottom of the bite block followed by a curved portion, wherein the oxygen administration channel extends parallel and adjacent to the straight portion of the tongue depressor, wherein the oxygen administration channel ends prior to the curved portion of the tongue depressor, wherein a length of the tongue depressor is between 40 mm and 140 mm;
wherein the shield, the bite block, and the oxygen administration channel are integrally formed;
administering oxygen through the oxygen administration channel; and
passing one of a bronchoscope or an endoscope through the primary instrument channel.

22. The method of claim 21, further comprising:
administering topical anesthesia to the patient through the oxygen administration channel.

* * * * *